(12) United States Patent
Roettger et al.

(10) Patent No.: US 9,668,827 B2
(45) Date of Patent: *Jun. 6, 2017

(54) COMPOSITE ORAL APPLIANCES AND METHODS FOR MANUFACTURE

(71) Applicant: Bite Tech, Inc., Norwalk, CT (US)

(72) Inventors: Mark Roettger, Lake Elmo, MN (US);
Robert C. Molhoek, Edina, MN (US);
Jon D. Kittelsen, Stillwater, MN (US);
Henry D. Cross, III, Murrells Inlet, SC (US); Paul A. Broadbent, Mill Valley, CA (US); Paul L. Bradshaw, Pembroke Pines, FL (US); Paul C. Belvedere, Edina, MN (US); William L. Ballanoff, Davie, FL (US)

(73) Assignee: BITE TECH, INC., Norwalk, CT (US)

( * ) Notice: Subject to any disclaimer, the term of this patent is extended or adjusted under 35 U.S.C. 154(b) by 480 days.

This patent is subject to a terminal disclaimer.

(21) Appl. No.: 14/044,600

(22) Filed: Oct. 2, 2013

(65) Prior Publication Data

US 2014/0026896 A1 Jan. 30, 2014

Related U.S. Application Data

(63) Continuation of application No. 12/484,216, filed on Aug. 26, 2009, now Pat. No. 8,567,408, which is a (Continued)

(51) Int. Cl.
*A63B 71/08* (2006.01)
*A61C 5/14* (2006.01)
*A61C 7/08* (2006.01)

(52) U.S. Cl.
CPC .............. *A61C 5/14* (2013.01); *A63B 71/085* (2013.01); *A61C 7/08* (2013.01)

(58) Field of Classification Search
CPC ....................................................... A61C 5/14
(Continued)

(56) References Cited

U.S. PATENT DOCUMENTS 257,038 A 4/1882 McMann
1,117,928 A 11/1914 Thurmond
(Continued)

FOREIGN PATENT DOCUMENTS

CA 1147583 6/1983
DE 480423 7/1929
(Continued)

OTHER PUBLICATIONS

Notification of Transmittal of the International Search Report and the Written Opinion of the ISA for related International Patent Application PCT/US2008/070020 filed Jul. 14, 2008.
(Continued)

*Primary Examiner* — Tarla Patel
(74) *Attorney, Agent, or Firm* — Billion & Armitage; Benjamin C. Armitage (57) ABSTRACT

Oral appliances adapted to for spacing the occlusal surfaces of the teeth of a user are disclosed. The oral appliances have an integral retention band interconnecting a first bite pad and a second bite pad. The first bite pad can include a first spacer and the second bite pad can include a second spacer that are configured to maintain the spacing of the occlusal surfaces of opposing teeth of a user during clenching or upon an impact to the jaw. Methods for the manufacture of composite oral appliances are also disclosed. The methods include forming a composite oral appliance over a model of a user's mouth.

14 Claims, 6 Drawing Sheets

Related U.S. Application Data continuation-in-part of application No. PCT/US2009/047295, filed on Jun. 14, 2009, and a continuation-in-part of application No. 10/460,886, filed on Jun. 12, 2003, now Pat. No. 8,074,658, which is a continuation-in-part of application No. 09/657,421, filed on Sep. 8, 2000, now Pat. No. 6,626,180.

(60) Provisional application No. 61/132,588, filed on Jun. 19, 2008.

(58) Field of Classification Search
USPC .... 128/846, 857, 859, 861–862; 433/2, 6, 9, 433/18–19
See application file for complete search history.

(56) References Cited

U.S. PATENT DOCUMENTS

| | | |
|---|---|---|
| 1,323,832 A | 12/1919 | Chige |
| 1,461,209 A | 7/1923 | Bridges |
| 1,470,888 A | 10/1923 | Smedley |
| 1,487,392 A | 3/1924 | Lee |
| 2,118,980 A | 5/1938 | Montgomery et al. |
| 2,257,709 A | 9/1941 | Anderson |
| 2,423,005 A | 6/1947 | Chaiken |
| 2,630,117 A | 3/1953 | Coleman |
| 2,643,652 A | 6/1953 | Cathcart |
| 2,659,366 A | 11/1953 | Savarese |
| 2,669,988 A | 2/1954 | Carpenter |
| 2,678,043 A | 5/1954 | Stark |
| 2,694,397 A | 11/1954 | Herms |
| 2,702,032 A | 2/1955 | Freedland |
| 2,708,931 A | 5/1955 | Freedland |
| 2,750,941 A | 6/1956 | Cathcart |
| 2,833,278 A | 5/1958 | Ross |
| 2,847,003 A | 8/1958 | Helmer et al. |
| 2,933,811 A | 4/1960 | Lifton |
| 2,966,908 A | 1/1961 | Cathcart et al. |
| 3,016,052 A | 1/1962 | Zubren |
| 3,058,462 A | 10/1962 | Greenblum |
| 3,073,300 A | 1/1963 | Berghash |
| 3,082,765 A | 3/1963 | Helmer |
| 3,107,667 A | 10/1963 | Moore |
| 3,124,129 A | 3/1964 | Grossberg |
| 3,126,002 A | 3/1964 | Owens |
| 3,203,417 A | 8/1965 | Helmer |
| 3,207,153 A | 9/1965 | Goldstein |
| 3,223,085 A | 12/1965 | Gores et al. |
| 3,247,844 A | 4/1966 | Berghash |
| 3,312,218 A | 4/1967 | Jacobs |
| 3,319,626 A | 5/1967 | Lindsay |
| 3,407,809 A | 10/1968 | Ross |
| 3,411,501 A | 11/1968 | Greenberg |
| 3,416,527 A | 12/1968 | Hoef |
| 3,448,738 A | 6/1969 | Berghash |
| 3,457,916 A | 7/1969 | Wolicki |
| 3,485,242 A | 12/1969 | Greenberg |
| 3,496,936 A | 2/1970 | Gores |
| 3,505,995 A | 4/1970 | Greenberg |
| 3,513,838 A | 5/1970 | Foderick et al. |
| 3,518,988 A | 7/1970 | Gores |
| 3,532,091 A | 10/1970 | Lerman |
| 3,682,164 A | 8/1972 | Miller |
| 3,692,025 A | 9/1972 | Greenberg |
| D228,048 S | 8/1973 | Miller |
| 3,768,465 A | 10/1973 | Helmer |
| 3,864,832 A | 2/1975 | Carlson |
| 3,916,527 A | 11/1975 | Linkow |
| 3,924,638 A | 12/1975 | Mann |
| 3,943,924 A | 3/1976 | Kallestad et al. |
| 4,030,493 A | 6/1977 | Walters et al. |
| 4,044,762 A | 8/1977 | Jacobs |
| 4,063,552 A | 12/1977 | Going et al. |
| 4,114,614 A | 9/1978 | Kesling |
| 4,185,817 A | 1/1980 | Peterson |
| 4,211,008 A | 7/1980 | Lerman |
| 4,330,272 A | 5/1982 | Bergersen |
| 4,337,765 A | 7/1982 | Zimmerman |
| 4,348,178 A | 9/1982 | Kurz |
| 4,376,628 A | 3/1983 | Aardse |
| 4,457,708 A | 7/1984 | Dufour |
| 4,490,112 A | 12/1984 | Tanaka et al. |
| 4,495,945 A | 1/1985 | Liegner |
| 4,519,386 A | 5/1985 | Sullivan |
| 4,568,280 A | 2/1986 | Ahlin |
| 4,591,341 A | 5/1986 | Andrews |
| 4,640,273 A | 2/1987 | Greene et al. |
| 4,651,356 A | 3/1987 | Zide |
| 4,671,766 A | 6/1987 | Norton |
| 4,672,959 A | 6/1987 | May et al. |
| 4,727,867 A | 3/1988 | Knoderer |
| 4,755,139 A | 7/1988 | Abbatte et al. |
| 4,763,791 A | 8/1988 | Halverson et al. |
| 4,765,324 A | 8/1988 | Lake, Jr. |
| 4,791,941 A | 12/1988 | Schaefer |
| 4,793,803 A | 12/1988 | Martz |
| 4,798,534 A | 1/1989 | Breads |
| 4,799,500 A | 1/1989 | Newbury |
| 4,810,192 A | 3/1989 | Williams |
| 4,838,283 A | 6/1989 | Lee, Jr. |
| 4,848,365 A | 7/1989 | Guarlotti et al. |
| 4,867,147 A | 9/1989 | Davis |
| 4,901,737 A | 2/1990 | Toone |
| 4,920,984 A | 5/1990 | Furumichi et al. |
| 4,944,947 A | 7/1990 | Newman |
| 4,955,393 A | 9/1990 | Adell |
| 4,976,618 A | 12/1990 | Anderson |
| 4,977,905 A | 12/1990 | Kittelsen et al. |
| 4,989,616 A | 2/1991 | Lee, Jr. |
| 5,031,611 A | 7/1991 | Moles |
| 5,031,638 A | 7/1991 | Castaldi |
| 5,063,940 A | 11/1991 | Adell et al. |
| 5,076,785 A | 12/1991 | Tsai |
| 5,082,007 A | 1/1992 | Adell |
| 5,103,838 A | 4/1992 | Yousif |
| 5,112,225 A | 5/1992 | Diesso |
| 5,117,816 A | 6/1992 | Shapiro et al. |
| D328,494 S | 8/1992 | Schwendeman et al. |
| 5,152,301 A | 10/1992 | Kittelsen et al. |
| 5,154,609 A | 10/1992 | George |
| 5,165,424 A | 11/1992 | Silverman |
| 5,174,284 A | 12/1992 | Jackson |
| 5,194,003 A | 3/1993 | Garay et al. |
| 5,194,004 A | 3/1993 | Bergersen |
| 5,203,351 A | 4/1993 | Adell |
| 5,234,005 A | 8/1993 | Kittelsen et al. |
| 5,235,991 A | 8/1993 | Minneman |
| 5,259,762 A | 11/1993 | Farrell |
| 5,277,203 A | 1/1994 | Hays |
| D343,928 S | 2/1994 | Kittelsen |
| 5,293,880 A | 3/1994 | Levitt |
| 5,297,960 A | 3/1994 | Burns |
| 5,299,936 A | 4/1994 | Ueno |
| 5,302,117 A | 4/1994 | Kraut et al. |
| 5,313,960 A | 5/1994 | Tomasi |
| 5,316,474 A | 5/1994 | Robertson |
| 5,320,114 A | 6/1994 | Kittelsen et al. |
| 5,323,787 A | 6/1994 | Pratt |
| 5,328,362 A | 7/1994 | Watson et al. |
| 5,336,086 A | 8/1994 | Simmen |
| 5,339,832 A | 8/1994 | Kittelsen et al. |
| 5,353,810 A | 10/1994 | Kittelsen et al. |
| 5,365,026 A | 11/1994 | Cromer, Jr. et al. |
| 5,365,946 A | 11/1994 | McMillan |
| 5,385,155 A | 1/1995 | Kittelsen et al. |
| 5,386,821 A | 2/1995 | Poterack |
| D356,188 S | 3/1995 | Kittelsen |
| 5,401,234 A | 3/1995 | Libin |
| 5,406,963 A | 4/1995 | Adell |
| 5,447,168 A | 9/1995 | Bancroft |
| 5,460,527 A | 10/1995 | Kittelsen |
| 5,469,865 A | 11/1995 | Minneman |
| 5,490,520 A | 2/1996 | Schaefer et al. |
| 5,511,562 A | 4/1996 | Hancock |

(56) References Cited

U.S. PATENT DOCUMENTS

| | | |
|---|---|---|
| 5,513,656 A | 5/1996 | Boyd, Sr. |
| 5,533,524 A | 7/1996 | Minneman |
| D373,421 S | 9/1996 | Brown |
| 5,566,684 A | 10/1996 | Wagner |
| 5,584,687 A | 12/1996 | Sullivan et al. |
| 5,586,562 A | 12/1996 | Matz |
| 5,590,643 A | 1/1997 | Flam |
| 5,592,951 A | 1/1997 | Castagnaro et al. |
| 5,624,257 A | 4/1997 | Farrell |
| 5,636,379 A | 6/1997 | Williams |
| 5,646,216 A | 7/1997 | Watson et al. |
| 5,649,534 A | 7/1997 | Briggs, III |
| 5,666,973 A | 9/1997 | Walter |
| 5,692,523 A | 12/1997 | Croll et al. |
| 5,715,840 A | 2/1998 | Hall |
| 5,718,243 A | 2/1998 | Weatherford et al. |
| 5,718,575 A | 2/1998 | Cross, III |
| 5,730,599 A | 3/1998 | Pak |
| 5,746,221 A | 5/1998 | Jones et al. |
| 5,752,822 A | 5/1998 | Robson |
| D397,442 S | 8/1998 | Kittelsen |
| 5,810,013 A | 9/1998 | Belfer |
| 5,816,255 A | 10/1998 | Fishman et al. |
| 5,819,744 A | 10/1998 | Stoyka, Jr. |
| 5,823,193 A | 10/1998 | Singer et al. |
| 5,823,194 A | 10/1998 | Lampert |
| 5,826,581 A | 10/1998 | Yoshida |
| 5,836,761 A | 11/1998 | Belvedere et al. |
| 5,865,619 A | 2/1999 | Cross, III et al. |
| 5,873,365 A | 2/1999 | Brown |
| 5,879,155 A | 3/1999 | Kittelsen |
| 5,915,385 A | 6/1999 | Hakimi |
| 5,921,240 A | 7/1999 | Gall |
| 5,921,241 A | 7/1999 | Belfer |
| 5,931,164 A | 8/1999 | Kiely et al. |
| 5,947,918 A | 9/1999 | Jones et al. |
| 5,970,981 A | 10/1999 | Ochel |
| 6,012,919 A | 1/2000 | Cross, III et al. |
| 6,036,487 A | 3/2000 | Westerman |
| 6,039,046 A | 3/2000 | Swartz et al. |
| 6,068,475 A | 5/2000 | Stoyka, Jr. |
| 6,082,363 A | 7/2000 | Washburn |
| 6,092,524 A | 7/2000 | Barnes, Sr. |
| 6,098,627 A | 8/2000 | Kellner et al. |
| 6,109,266 A | 8/2000 | Turchetti |
| 6,152,138 A | 11/2000 | Brown et al. |
| 6,164,278 A | 12/2000 | Nissani |
| 6,200,133 B1 | 3/2001 | Kittelsen |
| 6,222,524 B1 | 4/2001 | Salem et al. |
| 6,257,239 B1 | 7/2001 | Kittelsen et al. |
| 6,321,752 B1 | 11/2001 | Spottiswoode |
| 6,371,758 B1 | 4/2002 | Kittelsen |
| 6,423,049 B1 | 7/2002 | Tominaga et al. |
| 6,494,210 B1 | 12/2002 | Mams |
| 6,539,943 B1 | 4/2003 | Kittelsen et al. |
| 6,553,996 B2 | 4/2003 | Kittelsen et al. |
| 6,978,786 B2 | 12/2005 | Sabbagh |
| 7,404,404 B2 | 7/2008 | Lombardi |
| 8,567,408 B2 * | 10/2013 | Roettger ............... A63B 71/085 128/861 |
| 2003/0017874 A1 | 1/2003 | Jianfei et al. |
| 2003/0101999 A1 * | 6/2003 | Kittelsen ............... A63B 71/085 128/859 |
| 2004/0107970 A1 | 6/2004 | Kittelsen et al. |
| 2004/0250818 A1 | 12/2004 | Cook et al. |
| 2005/0109348 A1 | 5/2005 | Liu |
| 2006/0011204 A1 | 1/2006 | Maher |
| 2006/0046845 A1 | 3/2006 | Armand et al. |
| 2006/0169289 A1 | 8/2006 | Zacco |
| 2007/0136964 A1 | 6/2007 | Dawley |
| 2008/0138755 A1 | 6/2008 | Jansheski et al. |
| 2009/0114232 A1 | 5/2009 | Landi et al. |

FOREIGN PATENT DOCUMENTS

| | | |
|---|---|---|
| DE | 19732248 | 2/1998 |
| DE | 19844628 | 4/2000 |
| WO | 98/56305 | 12/1998 |
| WO | 9904722 | 2/1999 |
| WO | 03057097 | 7/2003 |

OTHER PUBLICATIONS

International Preliminary Report on Patentability for related International Patent Application PCT/US2008/070020 filed Jul. 14, 2008.

Notification of Transmittal of the Written Opinion of the ISA for related Internationals Patent Application PCT/US2008/074060 filed Aug. 22, 2008.

Notification of Transmittal of the International Search Report of the ISA for related International Patent Application PCT/US2008/074060 filed Aug. 22, 2008.

International Preliminary Report on Patentability for related International Patent Application PCT/US2008/074060 filed Aug. 22, 2008.

Notification of Transmittal of the International Search Report and the Written Opinion of the ISA for related International Patent Application PCT/US2009/047295 filed Jun. 14, 2009.

Notification of Transmittal of the International Search Report and the Written Opinion of the ISA for related International Patent Application PCT/US2009/047296 filed Jun. 14, 2009.

Notification of Transmittal of the International Search Report and the Written Opinion of the ISA for International Patent Application PCT/US2011/038778 filed Jun. 1, 2011.

Notification of Transmittal of the International Search Report and the Written Opinion of the ISA for International Patent Application PCT/US2011/038781 filed Jun. 1, 2011.

Tahara, Yasuaki DDS, et al. "Influence of Chewing and Clenching on Salivary Cortisol Levels as Indicator of Street". Journal of Prosthodontic; vol. 16, Issue 2 (2007): 129-135; Published online Feb. 20, 2007. © 2009 American College of Prosthodontists. Abstract only.

"Mouth Protectors: Give Your Teeth a Sporting Chance." Prepared in cooperation with the Academy of Sports Dentistry American Dental Association, (1985) Chicago, IL (7 pgs).

Smith, Stephen D., D.M.D. "Muscular Strength Correlated to Jaw Posture and the Temporomandibular Joint." NYS Dental Journal Vo. 44, No. 7 (1978): 278-282, Aug.-Sep. 1978.

May, W. B., D.D.S. "Reduction of Stress in the Chewing Mechanism— Part III." Basal Facts; vol. 3, No. 1:22-28.

Extended European Search Report for corresponding EP application No. 13178569.3 mailed on Mar. 12, 2015.

* cited by examiner

COMPOSITE ORAL APPLIANCES AND METHODS FOR MANUFACTURE

CROSS REFERENCE TO RELATED APPLICATIONS

The present application is a continuation of U.S. patent application Ser. No. 12/484,216, filed on Aug. 26, 2009, which is a continuation-in-part of International Application No. PCT/US2009/047295, filed on Jun. 14, 2009, which claims benefit and priority to U.S. Provisional Patent Application No. 61/132,588, filed on Jun. 19, 2008; the present application is also a continuation-in-part of U.S. patent application Ser. No. 10/460,886, filed on Jun. 12, 2003, and now issued as U.S. Pat. No. 8,074,658, which is a continuation-in-part of U.S. patent application Ser. No. 09/657,421, filed on Sep. 8, 2000, and now issued as U.S. Pat. No. 6,626,180, all of which is hereby incorporated by reference into the present disclosure.

BACKGROUND OF THE INVENTION

1. Summary of the Invention

The present inventions relate to mouthpieces and, more particularly, to oral devices for spacing the occlusal surfaces of the teeth of a user.

2. Description of the Related Art

Stress is a normal physiologic response and can be beneficial, maintaining alertness, focus, and efficiency. However, the body can become overloaded when stress becomes excessive (such as during the "fight or flight response") and both performance and health may be adversely affected. Teeth clench in response to elevated stress levels. This clenching mechanism may complete a circuit, as it were, and may signal the brain to begin a complex series of responses in the hypothalamic-pituitary-adrenal (HPA) axis. The HPA axis is a feedback loop signaling the release of hormones and affects various parts of the body. When someone is faced with a stressful situation, the hypothalamus releases the corticotropin-releasing hormone (CRH), which activates the pituitary gland to release adrenocorticotropin into the bloodstream. This triggers the adrenal glands to release epinephrine (adrenaline), norepinephrine (noradrenaline), and cortisol, all enabling the body's stress response. Epinephrine increases blood pressure, reaction time, and heart rate, and sends blood to the muscles. Cortisol releases glucose to supply the brain and muscles with immediate energy. The HPA axis communicates with regions of the brain, including the limbic system, which controls motivation and mood. It also communicates with the hippocampus, which has a vital role in memory formation, mood, and motivation. Other affected areas include body temperature, appetite, and pain control. Stress will also shut down hormonal systems, which affects growth, metabolism, and immunity. This serves as a useful short-term solution when the body must marshal its energies to confront or run from the source of stress. However, stress's interference outlives its usefulness and becomes detrimental when chronic.

Cortisol, the "stress hormone," is essentially the trigger for adrenaline. Cortisol belongs to a class of hormones called glucocorticoids, which affect almost every organ and tissue in the body. Scientists believe cortisol has hundreds of positive effects in the body but Cortisol's most important role may be to help the body respond properly to stress. Cortisol helps maintain blood pressure and cardiovascular function and is essential to normal functioning but needs to remain in proper balance. At excessively high levels, particularly for long periods, the whole endocrine system is affected negatively. High cortisol levels limit peripheral vision, decrease metabolism, cause fatigue, reduce muscle-building, and suppress the immune system. The results of tests showing, among other benefits, a significant increase in endurance as well as a marked reduction in Cortisol during stress. Therefore, a need exists for an apparatus that can interrupt the fight-or-flight signal by preventing the completion of the clenching mechanism.

Similar to other forms of stress, the natural inclination to clench the jaw during physical exertion is typically difficult to avoid. There are various theories as to why individuals clench their teeth in a wide variety of circumstances. One theory is that this is a primal reflex designed to protect the jaw from displacement or fracture. People still instinctively clench their teeth during aggression or physical activity. Accordingly, a need exists for an apparatus that may inhibit or prevent this clenching from completing "the circuit" that could signal the brain to begin a complex series of responses in the hypothalamic-pituitary-adrenal (HPA) axis.

It is also well recognized that the birthing process creates a tremendous amount of physiological and psychological stress upon the mother. The actual birthing process is very analogous to athletes as women about to give birth may very well clench their teeth during the exertion of labor. Therefore, a need exists for an apparatus that can interrupt the resulting physiological response by preventing the completion of the clenching mechanism.

It is also well recognized that military service generates a tremendous amount of physiological and psychological stress in the soldiers. This stress may result in regular clenching of the soldiers' teeth as they during the exertion of labor. This clenching can cause a number of changes that can detrimentally affect their physiology, psychology and judgment. Therefore, a need exists for an apparatus that preventing the completion of the clenching mechanism.

To be useful, an apparatus that prevents the completion of the clenching mechanism should be comfortable and unobtrusive and should not impede breathing or speaking to promote its use. However, many current designs for devices worn in the mouth have significant visual clues that they are being worn. They also frequently impede speech causing many users to have a lisp when they speak. Further, certain designs can significantly impede breathing through the mouth. Therefore, a need exists for apparatus that is both comfortable and unobtrusive when worn by a user.

For adequate fit and comfort, custom manufacture of certain oral appliance designs based on models of the users' teeth can be necessary. However, custom manufacture can be laborious and expensive. Therefore, a need exists for simple reproducible methods for manufacturing oral appliances that reduce the time and effort involved in the manufacture of custom oral appliances.

SUMMARY OF THE INVENTION

Apparatus and methods in accordance with the present invention may resolve many of the needs and shortcomings discussed above and will provide additional improvements and advantages as will be recognized by those skilled in the art upon review of the present disclosure.

In certain aspects, a composite oral appliance in accordance with the present invention may include: a body defining at least a first teeth fitment portion and a second teeth fitment portion including an integral retention band securing the first teeth fitment portion to the second teeth fitment portion with each of the first teeth fitment portion and the second teeth fitment portion configured to be secured over at least some teeth of a user and with each of the first teeth fitment portion and the second teeth fitment portion having a composite structure, the composite structure comprising at least an outer layer secured over an inner layer, the first teeth fitment portion further defining at least a first bite pad and the second teeth fitment portion defining at least a second bite pad, the composite structure at each of the first bite pad and the second bite pad comprising at least a spacer secured between an outer layer and an inner layer, the first bite pad and the second bite pad in positions to contact at least one of a molar and a premolar when worn by the user, an inner surface of the inner layer defining the shape of the teeth of a user.

In certain aspects, a method for manufacturing a composite oral appliance in accordance with the present invention may include: providing a model of one of an upper set of teeth and a lower set of teeth; forming an inner blank over at least a portion of the model; positioning a first spacer and a second spacer on an upper surface of the inner blank over at least one of a molar and a premolar of the model; forming an outer blank over at least a portion of the model; and securing the outer blank over the inner blank to form at least a first bite pad securing at least the first spacer and a second bite pad securing at least a second spacer to relatively secure at least a portion of the outer blank, the first spacer, the second spacer, and the inner blank together as a composite structure.

In certain aspects, a method for manufacturing a composite oral appliance in accordance with the present invention may further include: forming the inner blank, comprising: positioning the model in a forming chamber of a pressure forming apparatus; sealingly engaging an inner blank between the forming chamber and a high pressure chamber of the pressure forming apparatus; and generating a pressure differential between the forming chamber and the high pressure chamber to draw a portion of the blank over the model.

In certain aspects, a method for manufacturing a composite oral appliance in accordance with the present invention may further include: forming the outer blank, comprising: sealingly engaging an outer blank between the forming chamber and a high pressure chamber of the pressure forming apparatus; and generating a pressure differential between the forming chamber and the high pressure chamber to draw a portion of the blank over the first spacer and the second spacer and the first blank.

In certain aspects, a method for manufacturing a composite oral appliance in accordance with the present invention may further include: forming the outer blank, comprising: sealingly engaging an outer blank between the forming chamber and a high pressure chamber of the pressure forming apparatus; and generating a pressure differential between the forming chamber and the high pressure chamber to draw a portion of the blank over the first spacer and the second spacer and the first blank.

In certain aspects, a method for manufacturing a composite oral appliance in accordance with the present invention may further include: the step of forming a first tooth retention portion including the first spacer and a second tooth retention portion including the second spacer, and the first teeth fitment portion secured to the second teeth fitment portion by an integral retention band from the composite structure.

In certain aspects, a method for manufacturing a composite oral appliance in accordance with the present invention may further include: forming a first tooth retention portion including the first spacer and a second tooth retention portion including the second spacer from the composite structure; and securing with the first teeth fitment portion secured to the second teeth fitment portion with an integral retention band.

In certain aspects, a method for manufacturing a composite oral appliance in accordance with the present invention may include: providing a model of one of an upper set of teeth and a lower set of teeth; providing an inner material over the surface of at least one of a molar and a premolar of the model; positioning a first spacer and a second spacer on an upper surface of the inner material over at least one of a molar and a premolar on both a left side and a right side of the model; and forming an outer blank over at least a portion of the first spacer, the second spacer, the inner material and the model to relatively secure at least a portion of the outer blank, the first spacer, the second spacer, and the inner material together as a composite structure.

In certain aspects, a method for manufacturing a composite oral appliance in accordance with the present invention may further include: forming the outer blank, comprising: positioning the model in a forming chamber of a pressure forming apparatus; sealingly engaging a first blank between the forming chamber and a high pressure chamber of the pressure forming apparatus; and generating a pressure differential between the forming chamber and the high pressure chamber to form at least a portion of the first blank over the first spacer and the second spacer and the inner material.

In certain aspects, a method for manufacturing a composite oral appliance in accordance with the present invention may further include: forming a first tooth retention portion including the first spacer and a second tooth retention portion including the second spacer, and the first teeth fitment portion secured to the second teeth fitment portion by an integral retention band from the composite structure.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals designate the same or similar parts. Furthermore, when the terms "top," "bottom," "right," "left," "forward," "rearward," "front," "rear," "first," "second," "inside," "outside," "upper," "lower," "inferior," "superior," "anterior," "posterior," "proximal," "distal," "facial," "buccal," "oral," "lingual," "palatal," "distal," "mesial," and similar positional and/or relative terms are used, the terms should be understood to reference the structures shown in the drawings as they will typically be utilized by one skilled in the art or otherwise as would be recognized by one skilled in the art.

DETAILED DESCRIPTION OF THE INVENTION

The present inventions provide composite oral appliances 10 and methods for their manufacture. The figures generally illustrate embodiments of oral appliances 10 and methods for their manufacture in accordance with the present inventions. The particular exemplary embodiments of the composite oral appliances 10 illustrated in the figures have been chosen for ease of explanation and understanding of the various aspects of the present inventions. These illustrated embodiments are not meant to limit the scope of coverage but instead to assist in understanding the context of the language used in this specification and the appended claims. Accordingly, variations of composite oral appliances 10 including claimed aspects of the inventions different from the illustrated embodiments may be encompassed by the appended claims.

Various embodiments of oral appliances 10 in accordance with aspects of the present invention are illustrated throughout the figures for exemplary purposes. The illustrated oral appliances 10 include at least a first bite pad 12 and a second bite pad 14 interconnected by an integral connector band 20. The first bite pad 12 may be defined by, secured to, or integral with in the body 16. Similarly, the second bite pad 14 may be defined by, secured to, or integral with the body 16. The retention band 20 is typically integrally formed with the body 16 to at least interconnect the first bite pad 12 to the second bite pad 14. The body 16 may further define a first tooth fitment portion 116 and a second tooth fitment portion 216 (collectively, "fitment portions 116, 216") configured to generally configured to secure and/or position the first bite pad 12 and the second bite pad 14 (collectively, "bite pads 12, 14"), respectively, at the desired position relative to the occlusal surface of the teeth. In certain aspects, the first tooth fitment portion 116 and the second tooth fitment portion 216 may each form a channel 18 or at least a portion of a channel 18 to receive the teeth of a user. The channel 18 may solely extend in the area adjacent to the first bite pad 12 and the second bite pad 14 or may extend from the first bite pad 12 and the second bite pad 14 and around at least a portion of the retention band 20.

The first bite pad 12 includes at least a first spacer 32 and the second bite pad 14 includes at least a second spacer 34. The first bite pad 12 and the second bite pad 14 include a first spacer 32 and a second spacer 34, respectively, formed from a material selected to maintain the separation of the occlusal surfaces of the teeth during clenching or upon impact to the jaw. The bite pads 12, 14 may be configured to space the occlusal surface of one or more premolars and molars when the teeth of a user are clenched and may be generally configured to reduce or alleviate pressure at the temporomandibular joint when the user's teeth are clenched. In certain aspects, the bite pads 12, 14 of the composite oral appliance 10 may tend to direct the mandibular condyle downward from the articular fossa in response an attempt by a user to clench their teeth. In other aspects, the composite oral appliance 10 may tend to direct the mandibular condyle downward and forward from the articular fossa in response an attempt by a user to clench their teeth. The bite pads 12, 14 may also or alternatively be generally configured to protect the teeth and/or temporomandibular joint of a user when the user is subject to a blow to the jaw, head or otherwise receives an impacting force that may travel to or through the jaw.

FIGS. 1, 2, 3A, and 4A illustrate perspective views of exemplary embodiments of a composite oral appliance 10 configured to be positioned over the teeth of a user in accordance with aspects of the present inventions. As illustrated, the embodiment of composite oral appliance 10 may be configured to be received over at least some of the upper teeth or lower teeth of a user.

As illustrated, the body 16 of the oral appliance 10 defines a first tooth fitment portion 116, a second tooth fitment portion 216, a first bite pad 12, a second bite pad 16 and an integral connector band 20. The integral connector band 20 is configured to secure the first tooth fitment portion 116 to the second tooth fitment portion 216. The integral connector band 20 is shown configured to be positioned against any of the lingual, the palatal, the labial or the buccal surface of the gums and/or teeth. The first tooth fitment portion 116 has at least a first bite pad 12 defined as a thickened region of the body 16 and includes a first spacer 32 to maintain a desired thickness of the first bite pad 12 during clenching or upon an impact to the jaw. The second tooth fitment portion 216 also has at least a second bite pad 14 for positioning on the opposite side of the mouth that is defined as a thickened region of the body 16 and includes a second spacer 34 to maintain a desired thickness of the second bite pad 14 during clenching or upon an impact to the jaw. The first bite pad 12 and the second bite pad 14 are generally configured to be positioned over at least one of the lower molars on each side of a user's jaw when worn by a user. When the upper teeth and the lower teeth of a user are juxtaposed, the first bite pad 12 and the second bite pad 14 may be positioned between at least some of the upper molars and/or premolars and some of the lower molars and/or premolars. In certain embodiments, the first bite pad 12 and the second bite pad 14 may cover at least a portion of the second premolar and at least a portion of the first molar on each side of the jaw of a user.

The body 16 is generally formed as a thin layer of material. The material may be substantially rigid to permit the channel 18 to engage the teeth to mechanically secure the body 16 over at least a portion of the lower teeth of a user. Various portions of the body 16 may be composed of one or more layers of materials. These materials can include ethyl-vinyl acetate (EVA); thermoplastic polyolefin, various ethylene-based plasterers; various hydrocarbon resins (which are may be combined with EVA, thermoplastic polyolefin, or various ethylene-based elastomers), polycaprolactone (which may be combined with EVA), low-density polyethylene, high density poly-ethylene, polycarbonate and/or various polymers, laminates and other materials that will be recognized by those skilled in the art upon review of the present disclosure. In certain aspects, the composite material may be a pre-laminated sheet including a layer of polycarbonate bound to a layer of polyester urethane which is available under the trade name Durasoft® from the Scheu Dental Co. located in Iserlohn, Germany. Typically, these materials are selected with a durometer (hardness) of between 70 A to 96 A or between 55 D and 90 D.

The integral connector band 20 connects the first bite pad 12 to the second bite pad 14. In certain embodiments, the integral connector band 20 may secure the first tooth fitment portion 116 to the second tooth fitment portion 216. The integral connector band 20 is typically integrally formed with the body 16 along with the first bite pad 12 and the second bite pad 14. The integral connector band 20 is configured to extend as an arch around the lingual and/or palatal sides of at least the front teeth of a user. In an oral appliance 10 fitted for the lower teeth, the lower edge of the integral connector band 20 may in various configurations extend along, below or above the gum line of the user while the upper edge of the integral connector band 20 up to or below the incisal edge of the teeth. In an oral appliance 10 fitted for the upper teeth, the upper edge of the integral connector band 20 may in various configurations extend along, below or above the gum line of the user while the upper edge of the integral connector band 20 up to or above the incisal edge of the teeth. In certain embodiments, the integral connector band 20 may define a channel 18 to receive at least a portion of both the lingual/palatal and buccal/labial sides of a user's teeth and may thus wrap around and cover the incisal edge of the teeth. In certain aspects, this positioning of the integral connector band 20 can reduce the perceived obtrusiveness of the band within the mouth and can also reduce the impact on a user's speech.

The integral connector band 20 may take the form of a thin sheet of material having a thickness from between about 1.0 millimeter to about 6.0 millimeters. The band will typically take the form of a ribbon of material that is the same as the material of the body 16. The side or sides of the integral connector band 20 to be positioned against the teeth of a user may define one or more recesses 22. The recesses 22 may be shaped to receive the adjacent tooth. In certain aspects, this may permit the band to more tightly conform to the teeth of a user; may improve the comfort of the oral appliance 10; and may further secure the integral connector band 20 and oral appliance 10 within the mouth of a user. The integral connector band 20 will typically be formed from various polymers, various laminates, various natural materials or other synthetic materials as will be recognized by those skilled in the art upon review of the present disclosure and which will typically correspond with the material(s) of body 16.

At least the portion of the body 16 defining the first bite pad 12 and the second bite pad 14 has a composite structure. The composite structure including at least an outer layer 28 and an inner layer 26 of material secured to one another. The composite structure may also include a spacer 32, 34. The spacer 32, 34 may be positioned between the outer layer 28 and the inner layer 26. The spacer 32, 34 is typically formed from a material having a greater hardness than the material of the body 16. The spacer 32, 34 is typically of sufficient hardness to resist substantial penetration by the teeth and deformation as the teeth of a user are clenched. A material such as high density polyethylene or polypropylene may be used as well as other materials that will be recognized by those skilled in the art upon review of the present disclosure. The spacer 32, 34 may have a constant thickness from the front edge to the rear edge of the spacer 32, 34, it may be thicker at the front edge and be tapered to a thinner rear edge, it may have a thinner front edge and be tapered to a thicker rear edge, or it may be otherwise configured as will be recognized by those skilled in the art upon review of the present disclosure.

At least a portion of the inferior surface of the first tooth fitment portion 116 and the second tooth fitment portion 216 may conform to the shape of the teeth of the user. In certain aspects, one or more recesses 22 may be formed in the channel 18 of the tooth fitment portions 116, 216 to conform to and receive one or more teeth. The recesses 22 can enhance the fit, comfort and retention of the oral appliance 10 in the mouth of a user. At least a portion of a superior surface of the first tooth fitment portion 116 and the second tooth fitment portion 216 may also be shaped to correspond to the shape of the teeth of a user. In certain aspects, this shape may enhance the comfort and aesthetics of the oral appliance 10. The first tooth fitment portion 116 and the second tooth fitment portion 216 typically form channels 18 to receive the teeth. The channels 18 are elongated and are generally oriented along the mesial-distal axis. The at least a portion of a channel 18 may extend over one or more of the canines, premolars and/or molars on each side of the mouth. The channel 18 may be configured in shape of the teeth of the user. The channel 18 or the portion of a channel 18 may be defined by the inferior surface of the first tooth fitment portion 116 and second tooth fitment portion 216 to receive the teeth of the user. A channel occlusal surface 24 contacts at least a portion of the occlusal surface of the teeth. The channel occlusal surface 24 may be configured to conform to a least a portion of the occlusal surface of the user's teeth and may be configured to conform to the surfaces of all of the teeth received in the channel 18. To conform, typically, cavities will be formed in the channel occlusal surface 24 to correspond to at least the cusps of the occlusal surfaces. In certain aspects, this may more evenly distribute the force from clenching or an impact over the occlusal surface of the teeth and, among other things, may also improve retention and fitment.

When the teeth are engaged in the channel 18 in an oral appliance 10 configured to be secured over the lower teeth, a buccal body edge 144 of the first tooth fitment portion 116 and second tooth fitment portion 216 may extend below the lower gum-line of the user or some or all of the buccal body edge 144 may be configured to extend to a point above the lower gum-line of a user. When the teeth are engaged in the channel 18 in an oral appliance 10 configured to be secured over the upper teeth of a user, the buccal body edge 144 of the first tooth fitment portion 116 and second tooth fitment portion 216 may extend above the upper gum-line of the user or some or all of the buccal body edge 144 may be configured to extend to a point below the upper gum-line of a user.

The first tooth fitment portion 116 and the second tooth fitment portion 216 each form a mesial body edge 140. The mesial body edge 140 is typically configured to be positioned at or distal to the canines when the oral appliance is positioned in the mouth of a user. This can reduce the comfort of the device by eliminating coverage of the lingual side of the incisors that can cause irritation to the tongue of users.

The first tooth fitment portion 116 and the second tooth fitment portion 216 also each form a distal body edge 142. The distal body edge 142 is typically configured to be positioned at or mesial to the second molar or, when present, the third molar when the oral appliance is positioned in the mouth of a user.

At least the portion of the first tooth fitment portion 116 and the second tooth fitment portion 216 may define the first bite pad 12 and the second bite pad 14 (collectively "bite pads" 12, 14). The bite pads 12, 14 of oral appliance 10 may be configured to at least reduce pressure in the temporo-mandibular joint as the lower mandible is clenched. In certain aspects, the oral appliance 10 may tend to direct the mandibular condyle downward from the articular fossa in response an attempt by a user to clench their teeth. In other aspects, the oral appliance 10 may tend to direct the mandibular condyle downward and forward from the articular fossa in response an attempt by a user to clench their teeth.

The first bite pad 12 and the second bite pad 14 may be solely include a first spacer 32 and a second spacer 34 (collectively "spacers 32, 34"), respectively. Alternatively, the bite pads 12, 14 may be formed as a composite structure with each bite pad 12, 14 including one or more spacers 32, 34. When the bite pads 12, 14 are formed as a composite structure, the spacers 32, 34 may be embedded or encapsulated within one or more materials forming the bodies 116, 216. As such, the bite pads 12, 14 may include one or more of an outer layer 26 and an inner layer 26 of material secured over one or more spacers 32, 34. The spacers 32, 34 may be positioned between the outer layer 26 and the inner layer 26. The spacers 32, 34 are typically formed from a material having a greater hardness than the material of the outer layer 26 and inner layer 26. The spacers 32, 34 are typically of sufficient hardness to resist substantial penetration by the teeth and deformation as the teeth of a user are clenched. A material such as high density polyethylene or polypropylene may be used as well as other materials that will be recognized by those skilled in the art upon review of the present disclosure. The spacers 32, 34 may have a constant thickness from the front edge to the rear edge of the spacers 32, 34, it may be thicker at the front edge and be tapered to a thinner rear edge, it may have a thinner front edge and be tapered to a thicker rear edge, or it may be otherwise configured as will be recognized by those skilled in the art upon review of the present disclosure.

The bite pads 12, 14 are generally configured to define an external occlusal surface 22 to contact at least a portion of the occlusal surface of the opposing teeth and a channel occlusal surface 24 to contact the occlusal surfaces of the teeth relative to which the oral appliance 10 is secured. At least a portion of the channel occlusal surface 24 is coextensive with the channel occlusal surface 24 and may include the characteristics and features of the channel occlusal surface 24 as described above. The bite pads 12, 14 are generally configured to be positioned adjacent the occlusal surfaces of at least one of the canines, the premolars and the molars with at least one bite pad 12, 14 on each side of a user's mouth. Typically, the bite pads 12, 14 are positioned over the occlusal surfaces of at least one the premolars and at least one of the molars. In other aspects, the bite pads 12, 14 may be solely positioned over the occlusal surfaces of one or more molars.

In various aspects, the spacers 32, 34 of the bite pads 12, 14 may be configured to at least one of guide the mandible into a position that reduces or alleviates pressure at the temporomandibular joint during clenching and/or to transfer at least a portion of the force from an impact to the jaw to the cranium through the maxilla. The spacers 32, 34 are typically formed from a material having a sufficient hardness to resist substantial deformation when the teeth of a user are clenched while in contact with the spacer 32, 34. Accordingly, the spacers 32, 34 typically will have a durometer of between about 60 D to about 90 D although this may vary in certain embodiments of the invention.

Typically, the spacers 32, 34 are configured to be generally coextensive with the bite pads 12, 14. From a top view, the spacers 32, 34 may have an oblong shape and can be generally rectangular shape, a kidney shape, an oval shape, an egg shape or be otherwise shaped to extend along at least a portion of an occlusal surface of the underlying teeth as will be recognized by those skilled in the art upon review of the present disclosure. The spacers 32, 34 may define a mesial edge 40, a distal edge 42, a buccal edge 44, a lingual edge 46, a spacer channel surface 48, and a spacer outer surface 50. The spacers 32, 34 are generally configured to space the occlusal surface of opposing teeth when a clenching force is exerted by the user. For purposes of the present description, the length of the spacers 32, 34 extends between a mesial edge 40 and a distal edge 42 of the spacers 32, 34, the width of the spacers 32, 34 extends between a buccal edge 44 and a lingual edge 46 of the spacer, and the thickness of the spacers 32, 34 extends along the spacer channel surface 48 and an spacer channel surface 48 of the spacers 32, 34. Depending upon the particular application and particular products design, the length of the spacers 32, 34 is typically between about 10 millimeters to about 25 millimeters. The width of the spacers 32, 34 may be selected to contact or otherwise provide support between opposing teeth. The spacers 32, 34 are typically at least as wide as the distance between the cusps of individual adjacent teeth and the cusps of the opposing teeth. In certain aspects, the width may be as wide or wider than the width of the adjacent teeth or at least as wide as the spacing of the cusps of the teeth. Typically, they will be between about 5 millimeters and 15 millimeters. The thickness of the spacers 32, 34 generally establishes the distance the teeth will remain separated when the jaw is clenched or upon impact. The thickness of the spacers 32, 34 is typically between 0.25 millimeter and 2.5 millimeters. However, the spacers 32, 34 may have a constant thickness, a decreasing thickness along its length, or have their thickness otherwise varied along their length and/or width to reduces or alleviates pressure at the temporomandibular joint during clenching and/or to transfer at least a portion of the force from an impact to the jaw to the cranium through the maxilla. In certain aspects, the spacers 32, 34 may be configured as wedges with a thickness at their mesial ends that may approach 0.00 millimeters and a thickness at their distal ends between 0.25 millimeter and 2.5 millimeters. However, the mesial edge 40 of wedge shaped spacers 32, 34 typically has a thickness of at least 0.20 millimeters and the thickness at their distal ends of between 0.50 millimeters and 2.00 millimeters.

Figures 1, 2:
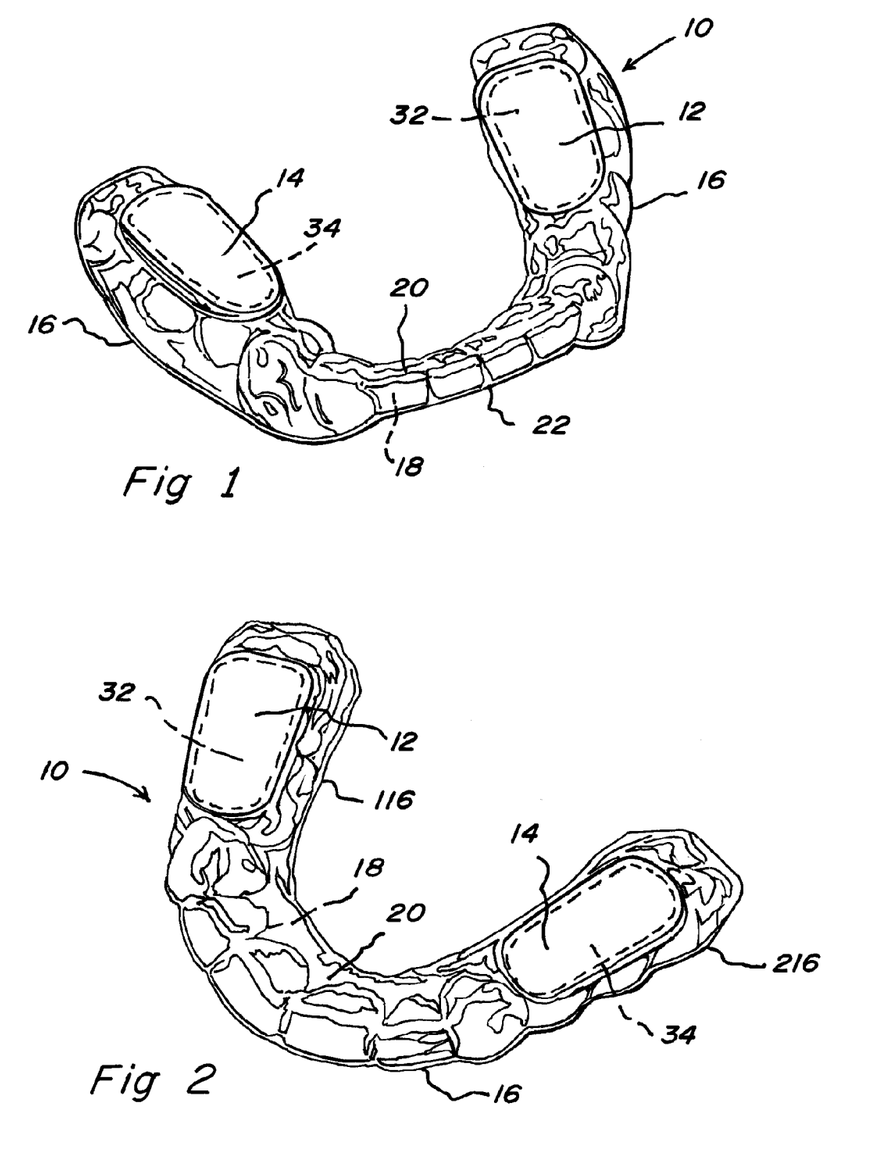
FIG. 1 illustrates a perspective view of an exemplary embodiment of a composite oral appliance generally configured to be positioned on the lower teeth of a user in accordance with aspects of the present inventions.
FIG. 2 illustrates a perspective view of an exemplary embodiment of a composite oral appliance generally configured to be positioned on the upper teeth of a user in accordance with aspects of the present inventions.
Figure 3A:
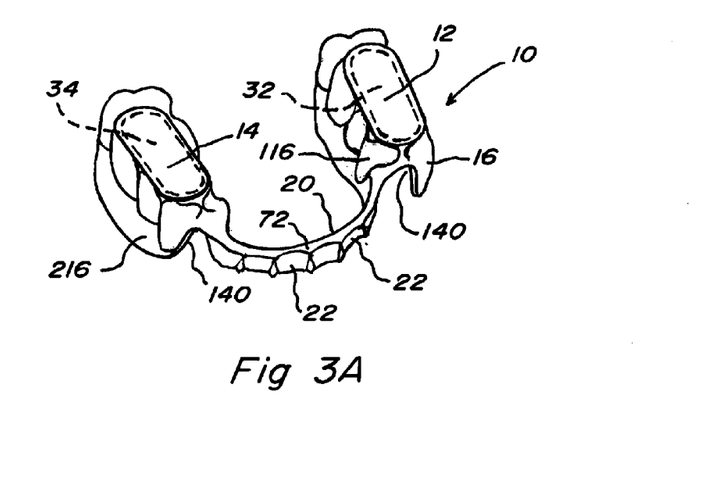
FIG. 3A illustrates a perspective view of an exemplary embodiment of a composite oral appliance generally configured to be positioned on the upper teeth of a user having a lingual strap in accordance with aspects of the present inventions.
Figure 3B:
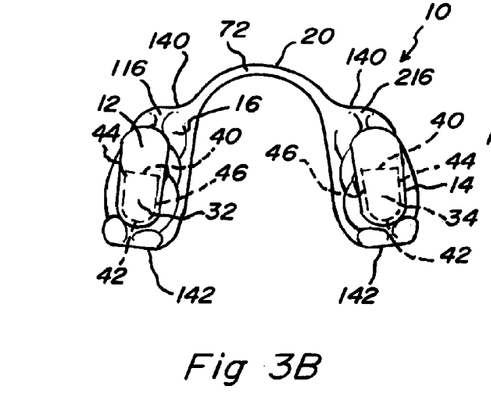
FIG. 3B illustrates a bottom view of an exemplary embodiment of a composite oral appliance generally configured to be positioned on the upper teeth of a user having a lingual strap in similar to the appliance illustrated in FIG. 3A.
Figure 3C:
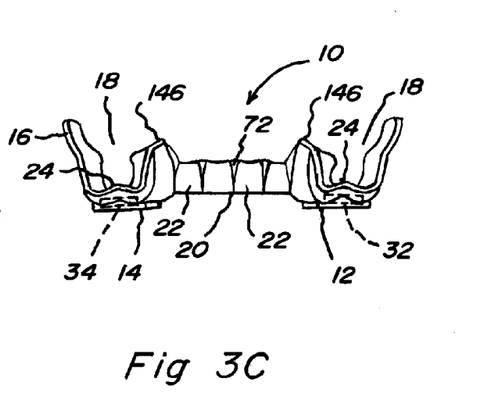
FIG. 3C illustrates a rear view of an exemplary embodiment of a composite oral appliance generally configured to be positioned on the upper teeth of a user having a lingual strap in similar to the appliance illustrated in FIG. 3A.

FIGS. 3A and 3C illustrate various features of an embodiment of an oral appliance 10 for positioning on upper teeth of a user. As illustrated, one or more molars and premolars may be positioned within the channel 18 defined by each of the first tooth fitment portion 116 and the second tooth fitment portion 216. The integral connector band 20 is configured to extend around the front of the mouth along the palatal surface of incisors and canines. The integral connector band 20 defines a plurality of recesses 22 shaped to receive a palatal surface of the incisors and canines of a user. The integral connector band 20 extends mesial from labial sides of the mesial body edges 140 of the first tooth fitment portion 116 and the second tooth fitment portion 216. The integral connector band 20 forms an arch 72 between the first tooth fitment portion 116 and the second tooth fitment portion 216 which is received against a palatal surface of at least the incisors and canines of a user. In certain embodiments, the arch 72 may be substantially coplanar in a transverse plane defined at one or more points along the lingual body edge 146 of the first tooth fitment portion 116 and the second tooth fitment portion 216. In certain embodiments configured for use on the lower teeth, the arch 72 may be positioned above a transverse plane defined at one or more points along the lingual body edge 146 of the first tooth fitment portion 116 and the second tooth fitment portion 216. In embodiments configured for use on the upper teeth, the arch 72 may be positioned below a transverse plane defined at one or more points along the lingual body edge 146 of the first tooth fitment portion 116 and the second tooth fitment portion 216.

The mesial body edge 140 of the first tooth fitment portion 116 may be positioned at mesial of the first premolar and the distal body edge 142 of the first tooth fitment portion 116 may be positioned at distal of the second molar to position the first tooth fitment portion 116 between at least the first premolar and second molar for exemplary purposes. Similarly, the mesial body edge 140 of the second tooth fitment portion 216 may be positioned at mesial of the first premolar and the distal body edge 142 of the second tooth fitment portion 216 may be positioned at distal of the second molar to position the second tooth fitment portion 216 between at least the first premolar and second molar for exemplary purposes. The mesial edge 40 of the first spacer 32 may be positioned over the mesio-occlusal surface of the second premolar and the distal edge 42 of the first spacer 32 is positioned at about the disto-occlusal surface of first molar on the left side of the mouth for exemplary purposes. The mesial edge 40 of the second spacer 34 is positioned over the mesio-occlusal surface of the second premolar and the distal edge of the second spacer 34 is positioned at about the disto-occlusal surface of first molar on the right side of the mouth for exemplary purposes. FIG. 3C illustrates a rear view of an oral appliance 10 with the integral connector band 20 and the channels 18 extending through the first tooth fitment portion 116 and the second tooth fitment portion 216.

Figure 4A:
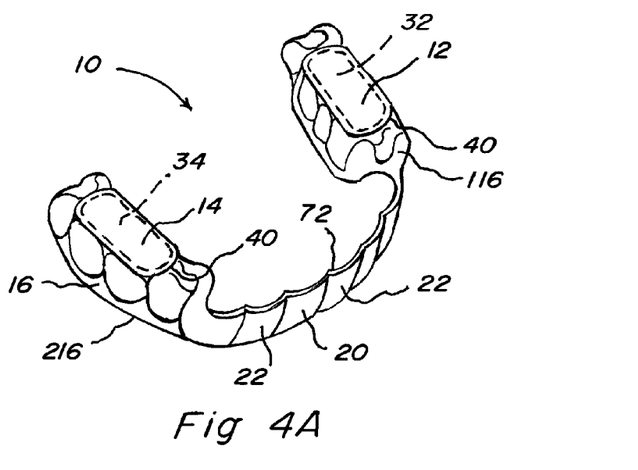
FIG. 4A illustrates a perspective view of an exemplary embodiment of a composite oral appliance generally configured to be positioned on the lower teeth of a user having a labial strap in accordance with aspects of the present inventions.
Figure 4B:
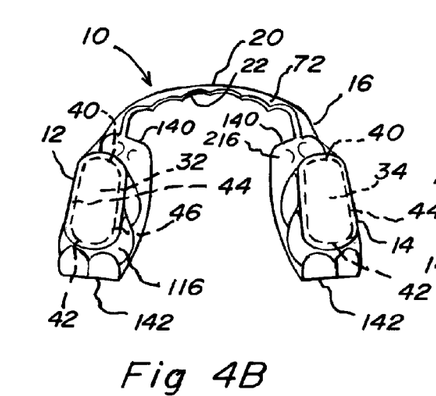
FIG. 4B illustrates a top view of an exemplary embodiment of a composite oral appliance generally configured to be positioned on the lower teeth of a user having a labial strap in similar to the appliance illustrated in FIG. 4A.
Figure 4C:
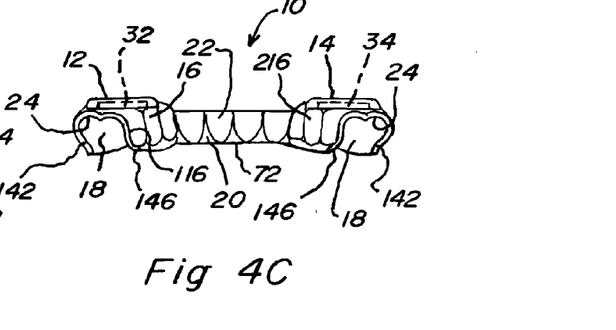
FIG. 4C illustrates a rear view of an exemplary embodiment of a composite oral appliance generally configured to be positioned on the lower teeth of a user having a labial strap in similar to the appliance illustrated in FIG. 4A.

FIGS. 4A and 4C illustrate various features of an embodiment of an oral appliance 10 for positioning on lower teeth of a user. As illustrated, one or more molars and premolars may be positioned within the channel 18 defined by each of the first tooth fitment portion 116 and the second tooth fitment portion 216. The integral connector band 20 is configured to extend around the front of the mouth along the palatal surface of incisors and canines. The integral connector band 20 defines a plurality of recesses 22 shaped to receive a labial surface of the incisors and canines of a user. The integral connector band 20 extends mesial from lingual sides of the mesial body edges 140 of the first tooth fitment portion 116 and the second tooth fitment portion 216. The integral connector band 20 forms an arch 72 between the first tooth fitment portion 116 and the second tooth fitment portion 216 which is received against a palatal surface of at least the incisors and canines of a user. In certain embodiments, the arch 72 may be substantially coplanar in a transverse plane defined at one or more points along the lingual body edge 146 of the first tooth fitment portion 116 and the second tooth fitment portion 216. In certain embodiments configured for use on the lower teeth, the arch 72 may be positioned above a transverse plane defined at one or more points along the lingual body edge 146 of the first tooth fitment portion 116 and the second tooth fitment portion 216. In embodiments configured for use on the upper teeth, the arch 72 may be positioned below a transverse plane defined at one or more points along the lingual body edge 146 of the first tooth fitment portion 116 and the second tooth fitment portion 216.

The mesial body edge 140 of the first tooth fitment portion 116 may be positioned at mesial of the first premolar and the distal body edge 142 of the first tooth fitment portion 116 may be positioned at distal of the second molar to position the first tooth fitment portion 116 between at least the first premolar and second molar for exemplary purposes. Similarly, the mesial body edge 140 of the second tooth fitment portion 216 may be positioned at mesial of the first premolar and the distal body edge 142 of the second tooth fitment portion 216 may be positioned at distal of the second molar to position the second tooth fitment portion 216 between at least the first premolar and second molar for exemplary purposes. The mesial edge 40 of the first spacer 32 may be positioned over the mesio-occlusal surface of the second premolar and the distal edge 42 of the first spacer 32 is positioned at about the disto-occlusal surface of first molar on the left side of the mouth for exemplary purposes. The mesial edge 40 of the second spacer 34 is positioned over the mesio-occlusal surface of the second premolar and the distal edge of the second spacer 34 is positioned at about the disto-occlusal surface of first molar on the right side of the mouth for exemplary purposes. FIG. 4C illustrates a rear view of an oral appliance 10 with the integral connector band 20 and the channels 18 extending through the first tooth fitment portion 116 and the second tooth fitment portion 216.

Figure 5A:
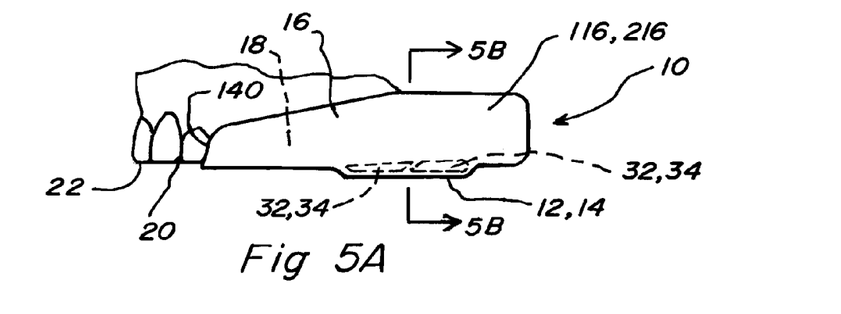
FIG. 5A illustrates a side view of an exemplary embodiment of a composite oral appliance positioned on the upper teeth of a user in accordance with aspects of the present inventions.

FIG. 5A illustrates a side view of an exemplary embodiment of a composite oral appliance positioned on the upper teeth of a user. The composite oral appliance 10 is secured over the upper teeth of a user with a channel 18 that extends over all of the upper teeth and defines recesses 22 receiving a portion of the palatal of the incisors and canines. The channel 18 extends from the disto-incisal of the canine to the disto-occlusal of at least the second molar for exemplary purposes. The integral retention band 20 extends around the palatal side (lingual side if the composite oral apparatus 10 was fit for lower teeth) of the incisors, canines and first pre-molar for exemplary purposes. Particularly, the integral retention band 20 extends from the lingual sides of the mesial body edges 140 of the first tooth fitment portion 116 and the second tooth fitment portion 216. As illustrated, the bite pad 12, 14 includes a spacer 32, 34 positioned within the tooth fitment portion 116, 216. The illustrated spacers 32, 34 have a thicker rear edge that tapers to a thinner front edge for exemplary purposes. Further, the bite pads 32, 34 are formed as two separate components that cooperate to form a wedge shaped bite pad 32, 34 for exemplary purposes.

Figure 5B:
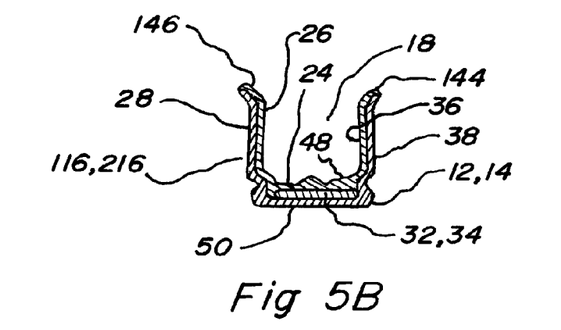
FIG. 5B illustrates a cross section through section 5B-5B of the composite oral appliance of FIG. 5A illustrating the composite structure.

FIG. 5B illustrates a cross section through section 3B-3B of the composite oral appliance of FIG. 5A illustrating the composite structure of each of the teeth fitment portions 116, 216. The channel 18 is shown extending downward from a buccal body edge 144 of the teeth fitment portions 116, 216 and around to the lingual body edge 146. The inner surface of channel 18 as illustrated is shaped to correspond with the profile of at least a portion of the teeth of a user. The inner shape may at least in part be formed in the inner material 36 which in the illustrated embodiment forms the inner layer 26 of the composite structure of the bite pad 32, 34 and/or teeth fitment portions 116, 216. The channel occlusal surface 24 is shaped to conform to the occlusal surfaces of the adjacent teeth. More particularly, the portion of the inner material 36 which defines the channel occlusal surface 24 is shaped to receive the occlusal surface of a molar. Similarly, the external occlusal surface 22 is shaped to receive at least a portion of the occlusal surfaces of the adjacent teeth. Among other things, this internal shaping may improve one or more of comfort, retention and shock/force dispersion. The outer surface the buccal wall and lingual wall of the outer layer 28 may be shaped to correspond to the shape of the underlying teeth which may improve comfort and the aesthetics of some embodiments.

The inner material 36 of the inner layer 26 may be secured to the outer material 38 of the outer layer 28 along at least a portion of the lingual wall and at least a portion of the buccal wall and along other portions of the teeth fitment portions 116, 216 where the inner material 36 of the inner layer 26 and the outer material 38 of the outer layer 28 come into contact. In various aspects, the materials 36, 38 of the layers 26, 28 may be heat fused, chemically linked, adhesively bonded, mechanically interconnected or otherwise secured to one another as will be recognized by those skilled in the art upon review of the present disclosure. At least a portion of the inner material 36 of the inner layer 26 in the lower portion of the channel 18 is at least in part positioned against and in some embodiments secured to spacer channel surface 48 of the spacers 32, 34. At least a portion of the outer layer 26 defining the channel occlusal surface 22 is positioned against and in some embodiments secured to a spacer outer surface 50 of the spacer 32, 34. In various aspects, the materials 36, 38 of the layers 26, 28 may be heat fused, chemically linked, adhesively bonded, mechanically interconnected or otherwise secured to the spacer surfaces 48, 50 as will be recognized by those skilled in the art upon review of the present disclosure. The spacers 32, 34 may be encapsulated between or otherwise secured to or within the inner materials 36 of the inner layer 26 and the outer material 38 of the outer layer 38 which form the teeth fitment portions 116, 216 of the oral appliance 10. At least a portion of the mounting portion 62 of the integral retention band 20 is secured to or integral with one or more of the inner layer 26 and the outer layer 28 of the teeth fitment portions 116, 216. In certain aspects, the integral retention band 20 may be integrally formed with one or both of the inner layer 26 and the outer layer 28. In other aspects, the integral retention band 20 may be secured at one or more ends to one or both of the inner layer 26 and the outer layer 28 of the teeth fitment portions 116, 216.

Figure 5C:
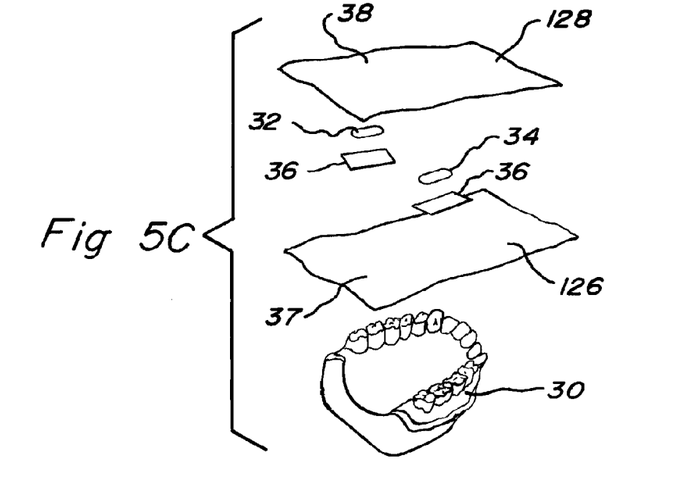
FIG. 5C illustrates an exploded perspective view exemplary embodiments of the components of the composite oral appliance as the components are assembled during manufacture in accordance with aspects of the present inventions.
Figure 5D:
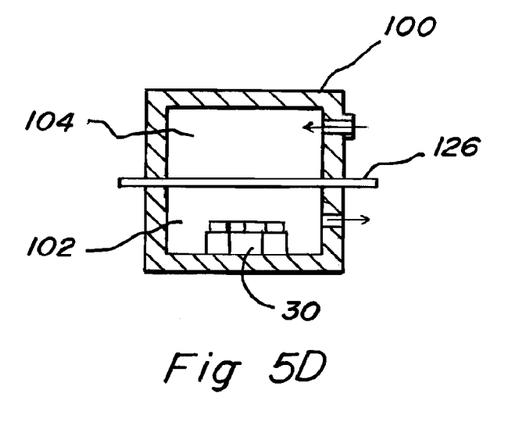
FIG. 5D illustrates a cross section of an exemplary embodiment of a sheet positioned to be formed over a model of an individual's dentition in accordance with aspects of the present inventions.
Figure 5E:
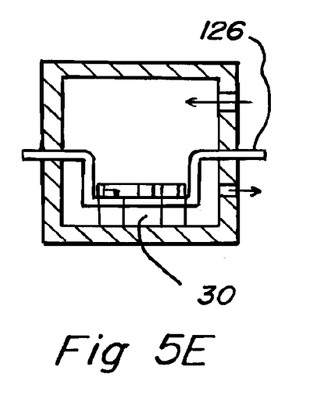
FIG. 5E illustrates a cross section of an exemplary embodiment of a sheet positioned being formed over a model of an individuals dentition in accordance with aspects of the present inventions.

FIG. 5C to 5E illustrate an exploded perspective view of other exemplary embodiments of the components of the oral appliance 10 and an exemplary forming apparatus 100 as the components may be assembled during manufacture. As illustrated, the method includes configuring and assembling at least an outer blank 128, a pair of spacers 32, 34, and an inner blank 126 to form an oral appliance 10. The components may also include an inner material 36 and an integral retention band 20. For each composite oral appliance 10, a model 30 of upper or lower teeth over which the oral appliance 10 will be formed is provided. The model 30 is typically formed by casting liquid stone or plaster in an impression of the upper or lower teeth of a user or into a standardized mold. Initially, the inner blank 126 is formed over the model 30 to assume the shape of the model 30 and, hence, the teeth of the user or standard on which the model 30 is based. The various components are positioned over the formed inner blank 126 on the model 30 and the outer blank 128 if formed over the model 30 and associated components to the interconnected components may then have the excess materials removed to produce a composite oral appliance 10.

A pressure forming apparatus 100 may be provided. The pressure forming apparatus 100 is generally configured to exert a force over a surface of the outer blank 128 to form it over the model 30 and associated components of the oral appliance 10. As will be recognized by those skilled in the art, a wide range of pressure forming apparatus may be used to form the outer blank 128 over the model 30 and may be applicable to the present methods. By way of non-limiting examples, the pressure forming apparatus 100 may be one or more of various devices for providing pneumatic pressure, hydraulic pressure, mechanical pressure or may use other forces to form the outer blank 128 to over the model 30 and associated components of the oral appliance 10.

In one step, the model 30 is placed in a forming chamber 102 of a pressure forming apparatus 100. An inner blank 126 of the material desired to form the inner layer 26 is provided. When the material is EVA, the inner blank 126 may have a thickness from about 1.0 millimeters to about 6.0 millimeters and is typically between 0.8 millimeters to about 4.0 millimeters in thickness. The inner blank 126 is secured in the pressure forming apparatus 100 to sealingly separate the forming chamber 102 from a high pressure chamber 104 as generally illustrated in FIG. 5D. The temperature of the inner blank 126 and/or the forming chamber 102 and high pressure chamber 104 as well as the model 30 may be raised to soften the inner blank 126. A pressure gradient is then generated between the high pressure chamber 104 and the forming chamber 102 to deform the inner blank 126 and force at least a portion of the inner blank 126 into the forming chamber 102 and against the model 30. As the inner blank 126 is forced against the model 30 in the forming chamber 102, a lower surface and, to varying degrees, an upper surface, of the inner blank 126 conforms to the shape of the model 30 as generally illustrated in FIG. 5E.

In another step, the inner material 36 may be positioned over the portion of the inner blank 126 onto which the spacers 32, 34 are to be secured. The inner material 36 may function to secure the spacers 32, 34 at the desired location on the model 30 during manufacture. As such, the inner material 36 may be placed on the inner blank 126 over at least one or more of the canines, premolars, and molars of the model 30 over at least a portion of the area on which the spacers 32, 34 will be secured. The inner material 36 may at least in part be selected to stabilize the position of the spacer 32, 34 on the inner blank 126 over the occlusal surfaces of one or more of the molars and/or premolars of the model 30 during manufacture.

The spacers 32, 34 are positioned at the desired location on an upper surface of or otherwise positioned over of the inner blank 126 and/or, when present, the inner material 36. In certain aspects, the spacers 32, 34 may be secured at the desired location on or in the inner material 36. The spacer channel surface 48 of the spacers 32, 34 is positioned against the inner blank 126 and/or, when present, the inner material 36.

The molded inner blank 126 and associated components are then positioned in the forming chamber 102 under the outer blank 128. When the outer material 38 is an EVA for example, the outer blank 128 may have a thickness from about 1.0 millimeters to about 6.0 millimeters and typically has a thickness between about 1.8 millimeters to about 4.0 millimeters. The outer blank 128 is secured in the pressure forming apparatus 100 to sealingly separate the forming chamber 102 from a high pressure chamber 104. The temperature of the outer blank 128 and/or the forming chamber 102 and high pressure chamber 104 as well as the model 30 may be raised to soften the outer blank 128. A pressure gradient is then generated between the high pressure chamber 104 and the forming chamber 102 to deform the outer blank 128 and force at least a portion of the outer blank 128 into the forming chamber 102 and against the spacers 32, 34, at least some of the inner material 36 and the model 30. Among other methodologies, the pressure gradient may be formed by increasing the pressure in the high pressure chamber 102 or forming at least a partial vacuum in the forming chamber 102. The temperatures and pressure differential may be selected to secure the outer blank 128 to the inner blank 126 and/or, when present, the inner material 36 where they come into contact. Similarly, the temperatures and pressure differential may be selected to secure the outer blank 128 and/or the inner blank 126 and/or, when present, the inner material 36 to the spacer 32, 34 where they come into contact with the spacer 32, 34. In certain embodiments, the temperature and pressure are configured to fuse the materials of at least two of the outer blank 128, the inner blank 126 and the spacer 32, 34. As the outer blank 128 is forced against the inner blank 126 and in the forming chamber 102, a lower surface of the outer blank 128 conforms to the shape of the spacers 32, 34, the inner blank 126 and/or, to some degree, depending upon its formulation and state, the inner material 36 when present. The integral retention band 20 may be secured to the oral appliance 10 prior to or subsequent to placement of the model 30 in the pressure forming apparatus 100. In methods where the integral retention band 20 is secured to the teeth fitment portions 116, 216, one or more ends of the integral retention band 20 may be secured to, in or between one or more of the outer blank 128, the spacers 32, 34, the inner blank 126 and, when present, the inner material 36. In certain aspects, the integral retention band 20 may be secured in a desired position relative to the model 30 such that the ends of the integral retention band 20 are or will be positioned within or on at least one of the inner sheet material 37 of the inner blank 126, the outer material 38 of the outer blank 128 or otherwise secured at the desired position in each of the first teeth fitment portion 116 and the second teeth fitment portion 216. As will be noted by those skilled in the art upon review of the present disclosure, various chemical treatments, adhesives, or other components may be integrated into the components or positioned between the layers to improve or alter the securing, bonding, connecting, linking and/or integration of the various components of the oral appliance 10.

After the over-molding process, the oral appliance 10 is removed from the model 30 and may be trimmed of excess material. In methods where the integral retention band 20 is integral with one or both of the first teeth fitment portion 116 and the second teeth fitment portion 216, the integral retention band 20 may be formed by cutting away and trimming the excess material of inner sheet 126 and outer sheet 128 from the model leaving the desired configuration of integral retention band 20 integrally connected to both the first teeth fitment portion 116 and the second teeth fitment portion 216. In certain aspects, on of either the inner sheet 126 or the outer sheet 128 may also be removed from at least a portion of the integral retention band 20 to reduce the thickness of the integral retention band.

Further, the oral appliance 10 may be mounted on an articulator and heated to form an impression of the opposing teeth on the surface opposite the cavity 18. Alternatively, the oral appliance 10 may be heated and manually articulated to form an impression of the opposing teeth on the surface opposite the cavity 18.

Figure 6A:
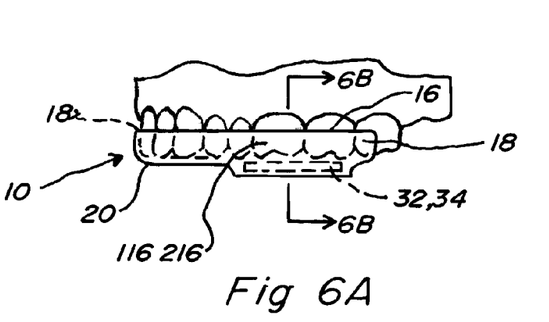
FIG. 6A illustrates a side view of an exemplary embodiment of a composite oral appliance positioned on the upper teeth of a user in accordance with aspects of the present inventions.

FIG. 6A illustrates a side view of an exemplary embodiment of a composite oral appliance positioned on the upper teeth of a user. The composite oral appliance 10 is secured over the upper teeth of a user with a channel 18 that extends in an arch around the mouth from the mesio-occlusal of the third molar to the mesio-occlusal of the third molar on the opposite side of the mouth. The channel occlusal surface 24 is shown configured to conform to the shape of the occlusal surface of the upper teeth. As illustrated, the bite pad 12, 14 includes spacers 32, 34 positioned within the first teeth fitment portion 116 and second teeth fitment portion 216. The illustrated spacers 32, 34 have a generally uniform thickness for exemplary purposes. Further, the bite pads 32, 34 are formed as a unitary component that is formed in a rectangular shape for exemplary purposes. The integral retention band 20 extends around both the labial and palatal sides of the incisors, canines and the pre-molar such that channel 18 is continuously formed in an arch 72 to receive at least all of the incisors and canines of the user for exemplary purposes.

Figure 6B:
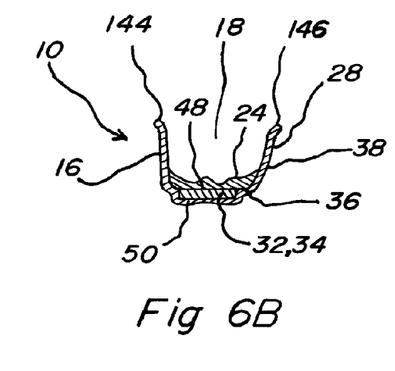
FIG. 6B illustrates a cross section through section 4B-4B of the composite oral appliance of FIG. 4A illustrating the composite structure.

FIG. 6B illustrates a cross section through section 6B-6B of the composite oral appliance of FIG. 6A illustrating the composite structure of this portion of the oral appliance 10. The channel 18 is shown extending downward from a buccal body edge 144 of the body 116, 216 and around to the lingual body edge 146. The inner surface of channel 18 as illustrated is shaped to correspond with the profile of at least a portion of the teeth of a user. The inner shape may at least in part be formed in the inner material 36 which in the illustrated embodiment forms the inner layer 26 of the composite structure of the bite pad 32, 34 and/or teeth fitment portions 116, 216. The channel occlusal surface 24 is shaped to conform to the occlusal surfaces of the adjacent teeth. More particularly, the portion of the inner material 36 which defines the channel occlusal surface 24 is shaped to receive the occlusal surface of a molar. Similarly, the external occlusal surface 22 is shaped to receive at least a portion of the occlusal surfaces of the adjacent teeth. Among other things, this internal shaping may improve one or more of comfort, retention and shock/force dispersion. The outer surface the buccal wall and lingual wall of the outer layer 28 may be shaped to correspond to the shape of the underlying teeth which may improve comfort and the aesthetics of some embodiments.

The inner material 36 of the inner layer 26 may be secured to the outer material 38 of the outer layer 28 along at least a portion of the lingual wall and at least a portion of the buccal wall and along other portions of the body 116, 216 where the inner material 36 of the inner layer 26 and the outer material 38 of the outer layer 28 come into contact. In various aspects, the materials 36, 38 of the layers 26, 28 may be heat fused, chemically linked, adhesively bonded, mechanically interconnected or otherwise secured to one another as will be recognized by those skilled in the art upon review of the present disclosure. At least a portion of the inner material 36 of the inner layer 26 in the lower portion of the channel 18 is at least in part positioned against and in some embodiments secured to spacer channel surface 48 of the spacers 32, 34. At least a portion of the outer layer 26 defining the channel occlusal surface 22 is positioned against and in some embodiments secured to a spacer outer surface 50 of the spacer 32, 34. In various aspects, the materials 36, 38 of the layers 26, 28 may be heat fused, chemically linked, adhesively bonded, mechanically interconnected or otherwise secured to the spacer surfaces 48, 50 as will be recognized by those skilled in the art upon review of the present disclosure. The spacers 32, 34 may be encapsulated between or otherwise secured to or within the inner materials 36 of the inner layer 26 and the outer material 38 of the outer layer 38 which form the bodies 116, 216 of the oral appliance 10. At least a portion of the integral retention band 20 may be secured between the inner layer 26 and the outer layer 28. Various other structures of the integral retention band 20 may extend into, through and between one or more layers 26, 28 of the bodies 116, 216 and into and through the spacers 32, 34 to secure the major connector relative to these elements.

Figure 6C:
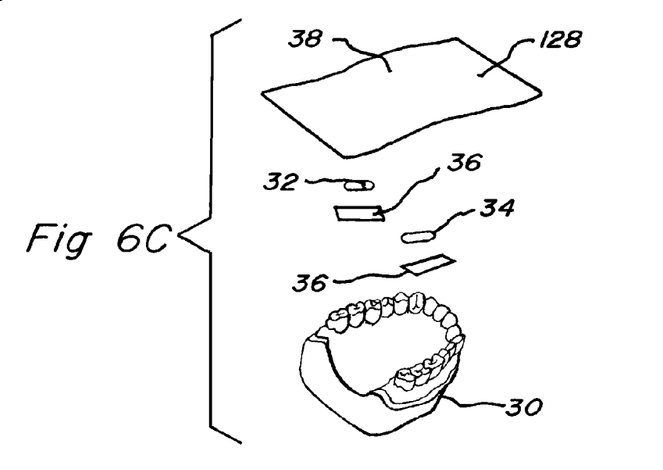
FIG. 6C illustrates an exploded perspective view exemplary embodiments of the components of the composite oral appliance as the components are assembled during manufacture in accordance with aspects of the present inventions.

FIG. 6C illustrates an exploded perspective view an exemplary embodiment of the components of the oral appliance 10 as the components may be assembled during manufacture. As illustrated, the method includes configuring and assembling at least an inner material 36, a pair of spacers 32, 34 and an outer blank 128 to form a composite oral appliance 10. The components may also include an integral retention band 20. For each oral appliance 10, a model 30 of upper or lower teeth over which the oral appliance 10 will be formed is provided. The model 30 is typically formed by casting liquid stone or plaster in an impression of the upper or lower teeth of a user or into a standardized mold. The various components are positioned over the model 30 and the outer blank 128 is formed over the model 30 and associated components to the interconnected components may then have the excess materials removed to produce a composite oral appliance 10.

In one step, the inner material 36 which will form the inner layer 26 over at least a portion of the channel occlusal surface 24 of the channel 18 is positioned on the model 30. Typically, the inner material 36 is placed over at least one or more of the canines, premolars, and molars of the model 30. The inner materials 36 will typically form at least a portion of inner layer 24 on the channel occlusal surface 24 of channel 18. The material 36 may be temporarily secured to the model by softening it with heat, by press fitting it onto the model 30 or otherwise as will be recognized by those skilled in the art depending on the material being used. The inner material 36 may be in a solid or a liquid form and may be a material such as one of various EVA based adhesives, various uncured polymers, various heat softening polymers, various light curable polymers or other materials as will be recognized by those skilled in the art upon review of the present disclosure. The inner material 36 is positioned at a desired location on the model 30. Typically, the inner material 36 is positioned on at least a portion of the occlusal surfaces of one or more of the molars and premolars. In certain embodiments, the inner material 36 is positioned on at least a portion of the occlusal surfaces at least the second premolar and the first molar of the model 30. The inner material 36 is generally selected and/or prepared to be formable over the teeth of model 30 as the outer blank 128 is made to conform to the model 30. It is desirable that the inner material 36 may satisfy the comfort and durability requirements for an inner surface of an oral appliance 10 as will be recognized by those skilled in the art upon review of the present disclosure. The inner material 36 may at least in part be selected to stabilize the position of the spacer 32, 34 on one or more of the molars and/or premolars of the model during manufacture.

The spacers 32, 34 are positioned at the desired location on an upper surface of or otherwise over the inner material 36. In certain aspects, the spacers 32, 34 may be secured at the desired location on or in the inner material 36. The spacer channel surface 48 of the spacers 32, 34 is positioned against the inner material 36. The inner material 36 may be made or may be provided as soft or tacky because of being a chemically treated, uncured, heated or softened or may have other properties or configurations to enable the spacers 32, 34 to be positioned relative to inner material 36 during manufacture as will be recognized by those skilled in the art upon review of the present disclosure. Prior to, during or after, the positioning of the spacers 32, 34, the integral retention band 20 may be positioned on the model 30. The integral retention band 20 may be positioned relative to the spacers 32, 34 and inner material 36 to facilitate their cooperation in securing the integral retention band 20 if required by the particular design of the oral appliance 10. In certain designs, the integral retention band 20 may alternatively secured to the other components at after the outer blank 128 is formed over the model 30 or after the excess material from the forming step has been removed.

Similar to the illustrative exemplary embodiment of FIGS. 5D and 5E, the model 30 is placed in a forming chamber 102 of a pressure forming apparatus 100 that uses pneumatic pressure to form the outer blank 128 over the model. The outer blank 128 of the outer material 38 desired to form the outer layer 26 is provided. When the outer material 38 is an EVA for example, the outer blank 128 may have a thickness from about 1.0 millimeters to about 6.0 millimeters and is typically between about 1.8 millimeters to about 4.0 millimeters. When the outer material 38 is a sheet of composite material including laminated an upper layer of polycarbonate and a lower layer of polyester urethane (the lower layer to be positioned against the teeth), the outer blank 128 may have a thickness of between about 1.0 millimeter and 6.0 millimeters with a typical thickness dimension being 0.8 mm of polycarbonate material and 1.0 millimeters of polyester urethane. The outer blank 128 is secured in the pressure forming apparatus 100 to sealingly separate the forming chamber 102 from a high pressure chamber 104. The temperature of the outer blank 128 and/or the forming chamber 102 and high pressure chamber 104 as well as the model 30 may be raised to soften the outer blank 128. A pressure gradient is then generated between the high pressure chamber 104 and the forming chamber 102 to deform the outer blank 128 and force at least a portion of the outer blank 128 into the forming chamber 102 and against the spacer 38, at least some of the inner material 36 and the model 30. Among other methodologies, the pressure gradient may be formed by increasing the pressure in the high pressure chamber 102 or forming at least a partial vacuum in the forming chamber 102. The temperatures and pressure differential may be selected to secure the outer blank 128 to the inner material 36 where they come into contact. Similarly, the temperatures and pressure differential may be selected to secure the outer blank 128 and/or the inner material 36 to the spacer 32, 34 where they come into contact with the spacer 32, 34. In certain embodiments, the temperature and pressure are configured to fuse the materials of at least two of the outer blank 128, the inner material 36 and the spacer 32, 34. As the outer blank 128 is forced against the model 30 in the forming chamber 102, a lower surface of the outer blank 128 conforms to the shape of the spacers 32, 34, the model 30, and, to some degree, depending upon its formulation and state, the inner material 36. The integral retention band 20 may be secured to the oral appliance 10 prior to or subsequent to placement of the model 30 in the pressure forming apparatus 100. In methods where the integral retention band 20 is secured at this step, the major connector may be secured in or between one or more of the outer blank 128, the spacers 32, 34 and the inner material 36. In certain aspects, the integral retention band 20 may be secured in a desired position relative to the model 30 such that the mounting portion 62 is or will be positioned within or on at least one of the inner material 36 and material of the outer blank 128 or otherwise secured at the desired position in each of the first teeth fitment portion 116 and the second teeth fitment portion 216. As will be noted by those skilled in the art upon review of the present disclosure, various chemical treatments, adhesives, or other components may be integrated into the components or positioned between the layers to improve or alter the securing, bonding, connecting, linking and/or integration of the various components of the oral appliance 10.

After the over-molding process, the oral appliance 10 is removed from the model 30 and may be trimmed of excess material. In methods where the integral retention band 20 is integral with one or both of the first teeth fitment portion 116 and the second teeth fitment portion 216, the integral retention band 20 may be formed by cutting away and trimming the excess material of inner sheet 126 and outer sheet 128 from the model leaving the desired configuration of integral retention band 20 integrally connected to both the first teeth fitment portion 116 and the second teeth fitment portion 216. In certain aspects, on of either the inner sheet 126 or the outer sheet 128 may also be removed from at least a portion of the integral retention band 20 to reduce the thickness of the integral retention band.

Further, the oral appliance 10 may be mounted on an articulator and heated to form an impression of the opposing teeth on the surface opposite the cavity 18. Alternatively, the oral appliance 10 may be heated and manually articulated to form an impression of the opposing teeth on the surface opposite the cavity 18.

The foregoing discussion discloses and describes merely exemplary embodiments of the present invention. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An oral appliance comprising:
   an oral appliance body including a first bite pad and a second bite pad interconnected by a retention band, the retention band integrally formed with the body;
   first and second tooth fitment portions, each forming at least a portion of a channel to receive teeth of a user and the first and second tooth fitment portions configured to position the bite pads relative to an occlusal surface of teeth; and
   two or more spacers co-extensive with each bite pad formed from a material having a sufficient hardness to resist substantial deformation when the teeth of a user are clenched while in contact with the two or more spacers;
   wherein the two or more spacers in cooperation have a thicker front edge and are tapered to a thinner rear edge or have a thinner front edge and are tapered to a thicker rear edge; and
   wherein the two or more spacers cooperate in a substantially vertical plane relative to tooth-contacting bite pad surfaces to form a wedge.

2. The oral appliance of claim 1, wherein the one or more spacers are formed from a material having a greater hardness than the material of the body.

3. The oral appliance of claim 1, wherein the retention band extends along the palatal surface of the front teeth only.

4. The oral appliance of claim 1, wherein the retention band extends along the labial surface of the front teeth only.

5. The oral appliance of claim 1, wherein each bite pad is co-extensive with a single spacer.

6. The oral appliance of claim 1, wherein each spacer is configured as a wedge.

7. The oral appliance of claim 1, wherein the spacers are of high density polyethylene or polypropylene.

8. The oral appliance of claim 1, wherein the retention band comprises one or more recesses defined in a side of the retention band and shaped to receive an adjacent tooth.

9. The oral appliance of claim 1, wherein the first and second bite pads are secured to the body.

10. The oral appliance of claim 1, wherein the first and second bite pads are integral with the body.

11. The oral appliance of claim 1, wherein each channel extends in the area adjacent to the first bite pad and second bite pad.

12. The oral appliance of claim 1, wherein each channel extends from the first bite pad and second bite pad and around to at least a portion of the retention band.

13. The oral appliance of claim 1, wherein the bite pads are configured to space an occlusal surface of one or more premolars and molars when the teeth of a user are clenched and are configured to reduce or alleviate pressure at the temporomandibular joint when the user's teeth are clenched.

14. The oral appliance of claim 1, wherein the one or more spacers are configured to at least one of guide the mandible into a position that reduces or alleviates pressure at the temporomandibular joint during clenching and to transfer at least a portion of the force from an impact to the jaw to the cranium through the maxilla.

* * * * *